(12) United States Patent
Fetscher et al.

(10) Patent No.: US 11,612,596 B2
(45) Date of Patent: *Mar. 28, 2023

(54) PHARMACEUTICAL FORMULATIONS COMPRISING CCR3 ANTAGONISTS

(71) Applicant: Alkahest, Inc., San Carlos, CA (US)

(72) Inventors: Alfred Fetscher, Betzenweiler (DE); Jochen Matthias Scher, Warthausen (DE)

(73) Assignee: Alkahest, Inc., San Carlos, CA (US)

( * ) Notice: Subject to any disclaimer, the term of this patent is extended or adjusted under 35 U.S.C. 154(b) by 246 days.

This patent is subject to a terminal disclaimer.

(21) Appl. No.: 16/861,473

(22) Filed: Apr. 29, 2020

(65) Prior Publication Data
US 2020/0253950 A1 Aug. 13, 2020

Related U.S. Application Data

(63) Continuation of application No. 16/235,905, filed on Dec. 28, 2018, now abandoned, which is a continuation of application No. 13/851,538, filed on Mar. 27, 2013, now Pat. No. 10,213,421.

(30) Foreign Application Priority Data

Apr. 4, 2012 (EP) .................................. 12163078

(51) Int. Cl.
| | | |
|---|---|---|
| A61K 31/4545 | (2006.01) | |
| A61K 9/16 | (2006.01) | |
| A61K 9/20 | (2006.01) | |
| A61K 9/28 | (2006.01) | |
| A61K 9/48 | (2006.01) | |
| A61K 9/00 | (2006.01) | |

(52) U.S. Cl.
CPC ........ *A61K 31/4545* (2013.01); *A61K 9/0053* (2013.01); *A61K 9/1617* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 9/2077* (2013.01); *A61K 9/284* (2013.01); *A61K 9/2813* (2013.01); *A61K 9/2853* (2013.01); *A61K 9/2866* (2013.01); *A61K 9/4858* (2013.01); *A61K 9/4866* (2013.01)

(58) Field of Classification Search
None
See application file for complete search history.

(56) References Cited

U.S. PATENT DOCUMENTS

| | | | |
|---|---|---|---|
| 4,289,781 A | 9/1981 | Bengtsson et al. | |
| 4,992,277 A | 2/1991 | Sangekar et al. | |
| 6,433,165 B1 | 8/2002 | Luly et al. | |
| 6,476,054 B1 | 11/2002 | Caldwell et al. | |
| 6,521,253 B1 | 2/2003 | Forsman et al. | |
| 7,041,316 B2 | 5/2006 | Chen | |
| 7,176,219 B2 | 2/2007 | Hayakawa et al. | |
| 7,544,806 B2 | 6/2009 | Anderskewitz et al. | |
| 7,759,365 B2 | 7/2010 | Martyres et al. | |
| 8,148,403 B2 | 4/2012 | Martyres et al. | |
| 8,153,660 B2 | 4/2012 | Martyres et al. | |
| 8,278,302 B2 | 10/2012 | Grundl et al. | |
| 10,213,421 B2 * | 2/2019 | Fetscher | A61K 9/4866 |
| 2004/0082788 A1 | 4/2004 | Brown | |
| 2005/0090504 A1 | 4/2005 | Gong et al. | |
| 2005/0182095 A1 | 8/2005 | Ting et al. | |
| 2007/0185075 A1 | 8/2007 | Bell et al. | |

(Continued)

FOREIGN PATENT DOCUMENTS

| | | |
|---|---|---|
| EP | 0468187 A2 | 1/1992 |
| JP | 2002501052 A | 1/2002 |

(Continued)

OTHER PUBLICATIONS

Abstract in English of JP2006137718, 2006.

(Continued)

*Primary Examiner* — Michael G. Hartley
*Assistant Examiner* — Lance W Rider
(74) *Attorney, Agent, or Firm* — Michael J. Blessent; Bret E. Field; Bozicevic, Field & Francis LLP

(57) ABSTRACT

The present invention relates to pharmaceutical compositions containing one or more compounds of formula 1

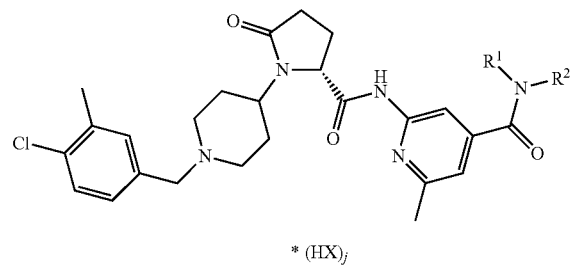

wherein
$R^1$ is H, $C_{1-6}$-alkyl, $C_{0-4}$-alkyl-$C_{3-6}$-cycloalkyl, $C_{1-6}$-haloalkyl;
$R^2$ is H, $C_{1-6}$-alkyl;
X is an anion selected from the group consisting of chloride or ½ dibenzoyltartrate;
j is 1 or 2; and processes for the preparation thereof, and their use to treat diseases connected with the CCR3 receptor.

16 Claims, No Drawings

(56) References Cited

U.S. PATENT DOCUMENTS

| | | |
|---|---|---|
| 2009/0123375 A1 | 5/2009 | Ambati |
| 2010/0261687 A1 | 10/2010 | Grundl et al. |
| 2010/0273782 A1 | 10/2010 | Ly et al. |
| 2011/0171295 A1 | 7/2011 | Shafee et al. |
| 2012/0264729 A1 | 10/2012 | Frank et al. |
| 2013/0023517 A1 | 1/2013 | Grundl et al. |
| 2013/0261153 A1 | 10/2013 | Nivens et al. |
| 2013/0261307 A1 | 10/2013 | Duran et al. |
| 2013/0266646 A1 | 10/2013 | Fetscher et al. |
| 2014/0135307 A1 | 5/2014 | Frank et al. |
| 2015/0099783 A1 | 4/2015 | Nivens et al. |

FOREIGN PATENT DOCUMENTS

| | | |
|---|---|---|
| JP | 2002501898 A | 1/2002 |
| JP | 2006137718 A | 6/2006 |
| JP | 2011-500780 A | 1/2011 |
| JP | 2011-241219 A | 12/2011 |
| WO | WO1996020699 A1 | 7/1996 |
| WO | WO2006083390 A2 | 8/2006 |
| WO | WO2006091671 A1 | 8/2006 |
| WO | WO2006095671 A1 | 9/2006 |
| WO | WO2007116313 A2 | 10/2007 |
| WO | WO2008092681 A1 | 8/2008 |
| WO | WO2009145721 A1 | 12/2009 |
| WO | WO2010052727 A1 | 5/2010 |
| WO | WO2010115836 A1 | 10/2010 |
| WO | WO2010123959 A2 | 10/2010 |
| WO | WO2012045803 A1 | 4/2012 |
| WO | WO2013149986 A1 | 10/2013 |
| WO | WO2013149987 A1 | 10/2013 |

OTHER PUBLICATIONS

Bachert et al., "Pharmacological Management of Nasal Polyposis," Drugs, 2005, vol. 65, No. 11, pp. 1537-1552.

Blanchard et al., "Eotaxin-3 and a Uniquely Conserved Gene-Expression Profile in Eosinophilic Esophagitis," The Journal of Clinical Investigation, 2006, vol. 116, No. 2, pp. 536-547.

De Lucca et al., "Discovery and Structure-Activity Relationship of N-(Ureidoalkyl)-Benzyl-Piperidines as Potent Small Molecule CC Chemokine Receptor-3 (CCR3) Antagonists," Journal of Medicinal Chemistry, vol. 45, 2002, pp. 3794-3804.

International Search Report and Written Opinion for PCT/EP2013/056867 dated Jun. 24, 2013.

Kozma, "Resolving Agents," CRC Handbook of Optical Resolutions Via Diastereomeric Salt Formation, Chapter 4, CRC Press LLC, Boca Raton, 2001, 47 pages.

Lin et al., "Preformulation Investigation I: Relation of Salt Forms and Biological Activity of an Experimental Antihypertensive," J. Pharm. Sci., 1972, pp. 1418-1422.

London et al., "Update and Review of Central Retinal Vein Occlusion," Current Opinion in Ophthalmology, vol. 22, 2011, pp. 159-165.

Sato et al., "Synthesis and structure-activity relations of N-{1-[(6-fluoro-2-naphthyl)methyl]piperidin-4-yl}benzamide derivatives as novel CCR3 antagonists," Bioorganic & Medicinal Chemistry, vol. 16, 2008, pp. 144-156.

Shaikh et al., "Stability of Pharmaceutical Formulations," Pak. J. Pharma. Sci., 1996, pp. 83-86.

Takeda et al., "CCR3 is a Target for Age-Related Macular Degeneration Diagnosis and Therapy," Nature, 2009, vol. 460, No. 7252, pp. 225-230.

Ting et al., "The synthesis of substituted bipiperidine amide compounds as CCR3 antagonist," Bioorganic & Medicinal Chemistry Letters, No. 15, 2005, pp. 1375-1378.

Wuts et al., "Protection for the Carboxyl Group," Greene's Protective Groups in Organic Synthesis, Ch. 5, 4th Edition, NY Wiley, 2007, pp. 553-559 and pp. 582-588.

Chapter 5, Pre-Formulation Research 1: Evaluation of Physiochemical Property of Drugs, Design and Evaluation of Oral Formulations, Feb. 10, 1995, Published by Yakugyou Jihou, Tokyo, Japan, p. 74-81.

Japanese Pharmaceutical Excipients 2007, Published by Yakuji Nippo Limited, Jul. 25, 2007, IPEC Japan International Pharmaceutical Excipients Council Japan, p. 92-93, and 222-227.

Sekar et al., Immediate Release Tablets of Telmisartan Using Superdisintegrant-Formulation, Evaluation and Stability Studies, Chem. Pharm. Bull. 56(4) 575-577 (2008).

Tiwari et al., Formulation and In-vitro Evaluation of Immediate release tablets of Drotaverine HCl, J. Chem. Pharm. Res., 2011, 3(4):333-341.

\* cited by examiner

PHARMACEUTICAL FORMULATIONS COMPRISING CCR3 ANTAGONISTS

The present invention relates to pharmaceutical compositions containing one or more compounds of formula 1

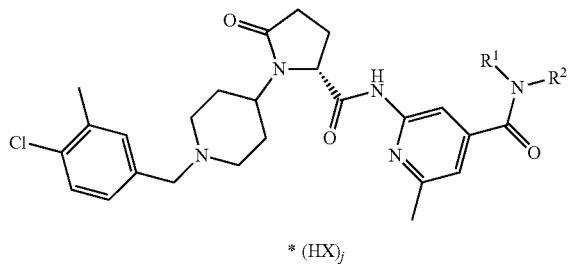

* (HX)$_j$ wherein
R$^1$ is H, C$_{1-6}$-alkyl, C$_{0-4}$-alkyl-C$_{3-6}$-cycloalkyl, C$_{1-6}$-haloalkyl;
R$^2$ is H, C$_{1-6}$-alkyl;
X is an anion selected from the group consisting of chloride or ½ dibenzoyltartrate;
j is 1 or 2; and
processes for the preparation thereof, and their use to treat diseases connected with the CCR3 receptor.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in Luster, New Eng. J Med., 338, 436-445 (1998); Rollins, Blood, 90, 909-928 (1997); Lloyd, Curr. Opin. Pharmacol., 3, 443-448 (2003); Murray, Current Drug Targets., 7, 579-588 (2006); Smit, Eur J Pharmacol., 533,277-88 (2006)).

There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP2) and melanoma growth stimulatory activity protein (MGSA) are chemotactic primarily for neutrophils and T lymphocytes, whereas the CC chemokines, such as RANTES, MIP-1a, MIP-1, the monocyte chemotactic proteins (MCP-1, MCP-2, MCP-3, MCP-4, and MCP-5) and the eotaxins (-1, -2, and -3) are chemotactic for, among other cell types, macrophages, T lymphocytes, eosinophils, mast cells, dendritic cells, and basophils. Also in existence are the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seventransmembrane-domain proteins (reviewed in Horuk, Trends Pharm. Sci., 15, 159-165 (1994); Murphy, Pharmacol Rev., 54 (2):227-229 (2002); Allen, Annu. Rev. Immunol., 25, 787-820 (2007)) which are termed "chemokine receptors." On binding their cognate ligands, chemokine receptors transduce an intracellular signal through the associated trimeric G proteins, resulting in, among other responses, a rapid increase in intracellular calcium concentration, activation of G-proteins, changes in cell shape, increased expression of cellular adhesion molecules, degranulation, promotion of cell migration, survival and proliferation. There are at least eleven human chemokine receptors that bind or respond to CC chemokines with the following characteristic patterns: CCR-1 (or "CKR-1" or "CC-CKR-1") [MIP-1a, MCP-3, MCP-4, RANTES] (Ben-Barruch, et al., Cell, 72, 415-425 (1993), Luster, New Eng. J. Med., 338, 436-445 (1998)); CCR-2A and CCR-2B (or "CKR-2A"/"CKR-2B" or "CC-CKR-2A"/"CC-CKR-2B") [MCP-1, MCP2, MCP-3, MCP-4, MCP-5] (Charo et al., Proc. Natl. Acad. Sci. USA, 91, 2752-2756 (1994), Luster, New Eng. J. Med., 338, 436-445 (1998)); CCR3 (or "CKR-3" or "CC-CKR-3") [eotaxin-1, eotaxin-2, RANTES, MCP-3, MCP-4] (Combadiere, et al., J. Biol. Chem., 270, 16491-16494 (1995), Luster, New Eng. J. Med., 338, 436-445 (1998)); CCR-4 (or "CKR-4" or "CC-CKR-4") [TARC, MIP-1a, RANTES, MCP-1] (Power et al., J. Biol. Chem., 270, 19495-19500 (1995), Luster, New Eng. J. Med., 338, 436-445 (1998)); CCR-5 (or "CKR-5" OR "CCCKR-5") [MIP-1a, RANTES, MIP-1p] (Sanson, et al., Biochemistry, 35, 3362-3367 (1996)); CCR-6 (or "CKR-6" or "CC-CKR-6") [LARC] (Baba et al., J. Biol. Chem., 272, 14893-14898 (1997)); CCR-7 (or "CKR-7" or "CC-CKR-7") [ELC] (Yoshie et al., J. Leukoc. Biol. 62, 634-644 (1997)); CCR-8 (or "CKR-8" or "CC-CKR-8") [1-309, TARC, MIP-1p] (Napolitano et al., J. Immunol., 157, 2759-2763 (1996), Bernardini et al., Eur. J. Immunol., 28, 582-588 (1998)); CCR-10 (or "CKR-10" or "CC-CKR-10") [MCP-1, MCP-3](Bonini et al, DNA and Cell Biol., 16, 1249-1256 (1997)); and CCR31 (or "CKR-11" or "CC-CKR-11") [MCP-1, MCP-2, MCP-4](Schweickart et al., J Biol Chem, 275 9550-9556 (2000)).

In addition to the mammalian chemokine receptors, the Decoy receptors CCX-CKR, D6 and DARC/Duffy as well proteins expressed by mammalian cytomegaloviruses, herpes viruses and poxviruses, exhibit binding properties of chemokine receptors (reviewed by Wells and Schwartz, Curr. Opin. Biotech., 8, 741-748 (1997); Comerford, Bioessays., 29(3):237-47 (2007)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR-4, CCR2, CCR3, CCR5 and CCR8, can act as co receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis, Grave's disease, chronic obstructive pulmonary disease, and atherosclerosis. For example, the chemokine receptor CCR3 is expressed among others on eosinophils, basophils, TH2 cells, alveolar macrophages, mast cells, epithelial cells, microglia cells, astrocytes and fibroblasts. CCR3 plays a pivotal role in attracting eosinophils to sites of allergic inflammation and in subsequently activating these cells. The chemokine ligands for CCR3 induce a rapid increase in intracellular calcium concentration, increased GTP exchange of G-proteins, increased ERK phosphorylation, enhanced receptor internalization, eosinophil shape change, increased expression of cellular adhesion molecules, cellular degranulation, and the promotion of migration. Accordingly, agents that inhibit chemokine receptors would be useful in such disorders and diseases. In addition, agents that inhibit chemokine receptors would also be useful in infectious diseases such as by blocking infection of CCR3 expressing cells by HIV or in preventing the manipulation of immune cellular responses by viruses such as cytomegaloviruses.

Therefore, CCR3 is an important target and antagonism of CCR3 is likely to be effective in the treatment of inflammatory, eosinophilic, immunoregulatory and infectious disorders and diseases (Wegmann, Am J Respir Cell Mol Biol., 36(1):61-67 (2007); Fryer J Clin Invest., 116(1):228-236 (2006); De Lucca, Curr Opin Drug Discov Devel., 9(4):516-524 (2006)).

It has been found and disclosed in WO 2010 115836 that the substituted piperidines of formula 1 are highly suitable as CCR3 antagonists, having less side effects, e.g. inhibition of norepinephrine (NET), dopamine (DAT) or serotonin reuptake transporters (5-HTT) as described by Watson P S, Bioorg Med Chem Lett., 16(21):5695-5699 (2006), or inhibition of 5HT2A, 5HT2C or Dopamine D2 receptors as described by De Lucca, J Med Chem., 48(6):2194-2211 (2005), or inhibition of the hERG channel as described by De Lucca, Curr Opin Drug Discov Devel., 9(4):516-524 (2006), or inhibition of the alpha1B adrenergic receptor.

Thus, these compounds of formula 1 could be used as a medicament in pharmaceutical formulations similar to those known from the prior art (List et al., Arzneiformen-lehre, Wissenschaftliche Verlagsgesellschaft mbH Stuttgart, 4.Auflage, p70ff).

From initial stability experiments with the compounds it became obvious, that the drug substance will require stabilizing effects due to the manufacturing process and/or the formulation ingredients to enable sufficient stability under standard conditions for medicaments according to the regulations of Drug Registration Authorities. In addition widely used standard manufacturing processes like direct compression or aqueous granulation could not be applied to the compound, due to the physical characteristics of the drug substance such as bulk density or deriving Hausner factor, electrostatic charging and surface adhesive properties. These characteristics may significantly influence key features such as flowability and compressibility, which are important for processing of the drug substance in order to manufacture a pharmaceutical dosage form.

TABLE 1

Hausner Factor and corresponding Flow Properties

| Hausner Factor | Flow Properties |
|---|---|
| 1.05-1.18 | Excellent |
| 1.14-1.19 | Good |
| 1.22-1.27 | Acceptable |
| 1.30-1.54 | Bad |
| 1.49-1.61 | Very bad |
| >1.67 | No flow |

The Hausner factor is the ratio of bulk volume to compacted volume, calculated by the formula bulk density/tapped density. Bulk density is measured according to Ph. Eur. 2.9.15 (European Pharmacopoeia, 4. Ed.) as poured density. The tapped density is measured according to Ph. Eur. 2.9.15 (see also Voigt R., Lehrbuch der pharmazeutischen Technologie [Textbook of Pharmaceutical Technology], Verlag Chemie, 5th Edition, page 148). The Hausner factor is a measure for the flowability/compressibility of powders and ideally should be close to 1.

Thus, the skilled artisan would have expected the need to find a new and inventive pharmaceutical formulation for compounds of formula 1, to prevent the drug substance in the formulation from degradation, especially hydrolytical cleavage which can be caused by air moisture and the water content of standard pharmaceutical excipients.

DETAILED DESCRIPTION OF THE INVENTION

A first object of the present invention is a pharmaceutical composition containing one or more compounds of formula 1

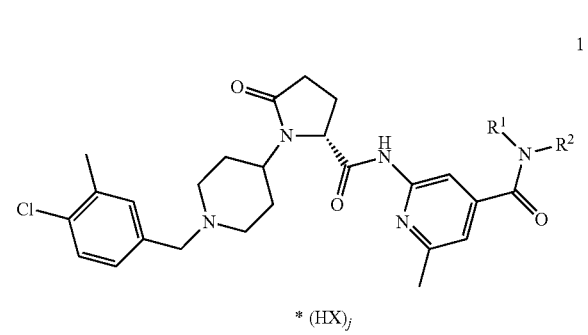

wherein
R$^1$ is H, C$_{1-6}$-alkyl, C$_{0-4}$-alkyl-C$_{3-6}$-cycloalkyl, C$_{1-6}$-haloalkyl;
R$^2$ is H, C$_{1-6}$-alkyl;
X is an anion selected from the group consisting of chloride or ½ dibenzoyltartrate;
j is 1 or 2; and
processes for the preparation thereof, and their use to treat diseases connected with the CCR3 receptor.

Preferred is a pharmaceutical composition containing one or more compounds of formula 1 wherein
R$^1$ is H, C$_{1-6}$-alkyl;
R$^2$ is H, C$_{1-6}$-alkyl;
X is an anion selected from the group consisting of chloride or ½ dibenzoyltartrate; and
j is 1 or 2.

Preferred is a pharmaceutical composition containing one or more compounds of formula 1 wherein
R$^1$ is H, Methyl, Ethyl, Propyl, Butyl;
R$^2$ is H, Methyl, Ethyl, Propyl, Butyl;
X is an anion selected from the group consisting of chloride or ½ dibenzoyltartrate, preferably chloride; and
j is 1 or 2, preferably 2.

Preferred is a pharmaceutical composition containing one or more compounds of formula 1 wherein
R$^1$ is H, Methyl, Ethyl, Propyl, Butyl;
R$^2$ is H, Methyl;
X is an anion selected from the group consisting of chloride or ½ dibenzoyltartrate, preferably chloride; and
j is 1 or 2, preferably 2.

Preferred is a pharmaceutical composition containing one or more compounds of formula 1 wherein
R$^1$ is H, Methyl;
R$^2$ is H, Methyl;
X is an anion selected from the group consisting of chloride or ½ dibenzoyltartrate, preferably chloride; and
j is 1 or 2, preferably 2.

Preferred is a pharmaceutical composition containing one or more of the examples 1, 2, 3, 4, 5, 6, 7, 8, 9 or 10 according to the table below as a hydrochloride. Furthermore preferred is a pharmaceutical composition containing one or more of the examples 1, 2, 3, 4, 5, 6, 7, 8, 9 or 10 according to the table below as a di-hydrochloride.

Another object of the present invention is the above pharmaceutical dosage form, wherein it is an orally deliverable dosage form.

Another object of the present invention is the above pharmaceutical dosage form which is in the form of a tablet (including a film coated tablet), capsule, pellets, powder or granules.

Another object of the present invention is the above pharmaceutical dosage form for use as medicament.

Another object of the present invention is the above pharmaceutical dosage form for the treatment of a disease or condition selected from respiratory diseases.

Another object of the present invention is the use of the above pharmaceutical dosage form for the preparation of a medicament for the treatment of a disease or condition selected from respiratory diseases.

Another object of the present invention is a process for the treatment and/or prevention of a disease or condition selected from respiratory diseases, characterized in that an effective amount of the above defined pharmaceutical dosage form is administered orally to a patient once, twice, thrice or several times daily.

Used Terms and Definitions

The term "about" means 5% more or less of the specified value. Thus, about 100 minutes could also be read as from 95 to 105 minutes.

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the first named subgroup is the radical attachment point, for example, the substituent "$C_{1-3}$-alkyl-aryl" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk is may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{1-n}$-haloalkyl", wherein n is an integer from 2 to n, either alone or in combination with another radical denotes an acyclic, saturated, branched or linear hydrocarbon radical with 1 to n C atoms wherein one or more hydrogen atoms are replaced by a halogene atom selected from among fluorine, chlorine or bromine, preferably fluorine and chlorine, particularly preferably fluorine. Examples include: $CH_2F$, $CHF_2$, $CF_3$.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

Dosage Forms/Ingredients

Solid pharmaceutical compositions ready for use/ingestion made from a compound of formula 1 comprise powders, granules, pellets, tablets, capsules, chewable tablets, dispersible tables, troches and lozenges. In detail:

Capsule formulations according to the invention comprise the powdery intermediate of a compound of formula 1, an intermediate blend comprising the powdery intermediate, pellets or granules obtained by conventional wet-, dry or hot-melt granulation or hot-melt extrusion or spray-drying of a suitable intermediate blend, filled in conventional capsules, e.g. hard gelatin or HPMC capsules.

The Capsule formulations from above may also comprise the powdery intermediate of a compound of formula 1 in a compacted form.

Capsule formulations according to the invention comprise the compound of formula 1 suspended or diluted in a liquid or mixture of liquids.

Tablet formulations according to the invention comprise such tablets obtained by direct compression of a suitable final blend or by tableting of pellets or granules obtained by conventional wet-, dry or hot-melt granulation or hot-melt extrusion or spray-drying of a suitable intermediate blend.

Another object of the present invention is a dosage form where a pH-adjusting or buffering agent is added for stability improvement of the active ingredient. The pH-adjusting/buffering agent may be a basic amino acid, which has an amino group and alkaline characteristics (isoelectric point, p: 7.59-10.76), such as e.g. L-arginine, L-lysine or L-histidine. The pH-adjusting/buffering agent may also be a basic sugar alcohol, like meglumine. A preferred pH-adjusting agent within the meaning of this invention is meglumin or L-arginine. L-arginine and meglumine have a particular suitable stabilizing effect on the compositions of this invention, e.g. by suppressing chemical degradation of compounds of formula 1.

Thus, in an embodiment, the present invention is directed to a pharmaceutical composition (e.g. an oral solid dosage form, particularly a tablet) comprising a compound of formula 1 and L-arginine or meglumine for stabilizing the composition, particularly against chemical degradation; as well as one or more pharmaceutical excipients.

Suitably the pharmaceutical excipients used within this invention are conventional materials such as cellulose and its derivates, D-mannitol, dibasic calcium phosphate, corn starch, pregelatinized starch as a filler, copovidone as a binder, crospovidone as disintegrant, magnesium stearate as a lubricant, colloidal anhydrous silica as a glidant, hypromellose, polyvinyl alcohol as film-coating agents, polyethylene glycol as a plasticizer, titanium dioxide, iron oxide red/yellow as a pigment, and talc, etc.

In detail pharmaceutical excipients can be a first and second diluent, a binder, a disintegrant and a lubricant; an additional disintegrant and an additional glidant are a further option.

Diluents suitable for a pharmaceutical composition according to the invention are cellulose powder, microcrystalline cellulose, lactose in various crystalline modifications, dibasic calciumphosphate anhydrous, dibasic calciumphosphate dihydrate, erythritol, low substituted hydroxypropyl cellulose, mannitol, starch or modified starch (eg pregelatinized or partially hydrolysed) or xylitol. Among those diluents dibasic calciumphosphate anhydrous and microcrystalline cellulose are preferred.

Diluents preferred as the second diluent are the above mentioned diluents dibasic calciumphosphate anhydrous and microcrystalline cellulose.

Lubricants suitable for a pharmaceutical composition according to the invention are talc, polyethyleneglycol, calcium behenate, calcium stearate, sodium stearylfumarate, hydrogenated castor oil or magnesium stearate. The preferred lubricant is magnesium stearate.

Binders suitable for a pharmaceutical composition according to the invention are copovidone (copolymerisates of vinylpyrrolidon with other vinylderivates), hydroxypropyl methylcellulose (HPMC), hydroxypropylcellulose (HPC), polyvinylpyrrolidon (povidone), pregelatinized starch, stearic-palmitic acid, low-substituted hydroxypropylcellulose (L-HPC), copovidone and pregelatinized starch being preferred. The above mentioned binders pregelatinized starch and L-HPC show additional diluent and disintegrant properties and can also be used as the second diluent or the disintegrant.

Disintegrants suitable for a pharmaceutical composition according to the present invention are corn starch, crospovidone, polacrilin potassium, croscarmellose sodium, low-substituted hydroxypropylcellulose (L-HPC) or pregelatinized starch; preferably croscarmellose sodium.

As an optional glidant colloidal silicon dioxide can be used.

An exemplary composition according to the present invention comprises the diluent dibasic calciumphosphate, microcrystalline cellulose as a diluent with additional disintegrating properties, the binder copovidone, the disintegrant croscarmellose sodium, and magnesium stearate as the lubricant.

Typical pharmaceutical compositions comprise (% by weight)

| | |
|---|---|
| 10-50% | active ingredient, |
| 20-88% | diluent 1, |
| 5-50% | diluent 2, |
| 1-5% | binder, |
| 1-15% | disintegrant, and |
| 0.1-5% | lubricant. |

Preferred pharmaceutical compositions comprise (% by weight)

| | |
|---|---|
| 10-50% | active ingredient, |
| 20-75% | diluent 1, |
| 5-30% | diluent 2, |
| 2-30% | binder, |
| 1-12% | disintegrant, and |
| 0.1-3% | lubricant. |

Preferred pharmaceutical compositions comprise (% by weight)

| | |
|---|---|
| 10-90% | active ingredient, |
| 5-70% | diluent 1, |
| 5-30% | diluent 2, |
| 0-30% | binder, |
| 1-12% | disintegrant, and |
| 0.1-3% | lubricant. |

Preferred pharmaceutical compositions comprise (% by weight)

| | |
|---|---|
| 10-50% | active ingredient, |
| 20-75% | diluent 1, |
| 5-30% | diluent 2, |
| 2-30% | binder, |
| 0.5-20% | buffering agent, |
| 1-12% | disintegrant, and |
| 0.1-3% | lubricant. |

Preferred pharmaceutical compositions comprise (% by weight)

| | |
|---|---|
| 30-70% | active ingredient, |
| 20-75% | diluent 1, |
| 5-30% | diluent 2, |
| 2-30% | binder, |
| 0.5-20% | buffering agent, |
| 1-12% | disintegrant, and |
| 0.1-3% | lubricant. |

Preferred pharmaceutical compositions comprise (% by weight)

| | |
|---|---|
| 30-70% | active ingredient, |
| 10-75% | diluent 1, |
| 5-30% | diluent 2, |
| 0-30% | binder, |
| 0.5-30% | buffering agent, |
| 1-12% | disintegrant, and |
| 0.1-3% | lubricant. |

Preferred pharmaceutical compositions comprise (% by weight)

| | |
|---|---|
| 30-70% | active ingredient, |
| 10-75% | diluent 1, |
| 5-30% | diluent 2, |
| 0.5-30% | buffering agent, |
| 1-12% | disintegrant, and |
| 0.1-3% | lubricant. |

Pharmaceutical compositions containing 10-90% of active ingredient, preferably 30-70% active ingredient (% by weight) are preferred.

A tablet formulation according to the invention may be uncoated or coated, e.g. film-coated, using suitable coatings known not to negatively affect the dissolution properties of the final formulation. For instance the tablets can be provided with a seal coat for protection of the patients environment and clinical staff as well as for moisture protection purposes by dissolving a high molecular weight polymer as polyvinylpyrrolidone or polyvinyl alcohol or hydroxypropyl-methylcellulose together with plasticizers, lubricants and optionally pigments and tensides in water or organic solvent as acetone and spraying this mixture on the tablet cores inside a coating equipment as a pan coater or a fluidized bed coater with wurster insert.

Additionally, agents such as beeswax, shellac, cellulose acetate phthalate, polyvinyl acetate phthalate, zein, film forming polymers such as hydroxypropyl cellulose, ethylcellulose and polymeric methacrylates can be applied to the tablets, provided that the coating has no substantial effect on the disintegration/dissolution of the dosage form and that the coated dosage form is not affected in its stability.

After the dosage form is film-coated, a sugar coating may be applied onto the sealed pharmaceutical dosage form. The sugar coating may comprise sucrose, dextrose, sorbitol and the like or mixtures thereof. If desired, colorants or opacifiers may be added to the sugar solution.

Solid formulations of the present invention tend to be hygroscopic. They may be packaged using PVC-blisters, PVDC-blisters or a moisture-proof packaging material such as aluminum foil blister packs, alu/alu blister, transparent or opaque polymer blister with pouch, polypropylene tubes, glass bottles and HDPE bottles optionally containing a child-resistant feature or may be tamper evident. The primary packaging material may comprise a desiccant such as molecular sieve or silica gel to improve chemical stability of the active ingredient (API). Opaque packaging such as colored blister materials, tubes, brown glass bottles or the like can be used to prolong shelf life of the API by reduction of photo degradation.

Dosages

A dosage range of the compound of formula 1 is usually between 100 and 1000 mg, in particular between 200 and 900 mg, 300 and 900 mg or 350 and 850 mg or 390 and 810 mg. It is possible to give one or two tablets, preferred are two tablets for a daily oral dosage of 100, 200, 300, 350, 400, 450, 500, 550, 600, 650, 700, 750, 800, 850, 900 mg, preferably 350, 400, 450, 750, 800, 850.

The dosages range can be achieved by one tablet or by two tablets; preferably two tablets are administered, each containing half of the dosage.

The application of the active ingredient may occur up to three times a day, preferably one or two times a day. Particular dosage strengths are 400 mg or 800 mg.

Methods of Production

Direct Compression

Due to the bad flowability properties of the drug substance and the high Hausner factor of approx 1.40 a direct compression process to produce tablets is not feasible. Therefore a granulation process (wet or dry granulation) has to be performed.

Wet Granulation

In the wet granulation process the granulation liquid is a solvent such as water, ethanol, methanol, isopropanol, acetone, preferably ethanol, and contains a binder such as copovidone. The solvent is a volatile component, which does not remain in the final product. The active ingredient and the other excipients with exception of the lubricant are premixed and granulated with the granulation liquid using a high shear granulator. The wet granulation step is followed by an optional wet sieving step, drying and dry sieving of the granules. For example a fluid bed dryer can then be used for drying.

The dried granules are sieved through an appropriate sieve. After addition of the other excipients with exception of the lubricant the mixture is blended in a suitable conventional blender such as a free fall blender followed by addition of the lubricant such as magnesium stearate and final blending in the blender.

Thus an exemplary wet granulation process for the preparation of a pharmaceutical composition according to the present invention comprises a. dissolving a binder such as copovidone in a solvent such as ethanol at ambient temperature to produce a granulation liquid;

b. blending a compound of formula 1, a diluent, and a disintegrant in a suitable mixer, to produce a pre-mix;

c. moistening the pre-mix with the granulation liquid and subsequently granulating the moistened pre-mix for example in a high shear mixer;

d. optionally sieving the granulated pre-mix through a sieve with a mesh size of at least 1.0 mm and preferably 3 mm;

e. drying the granulate at about 40-75° C. and preferably 55-65° C. inlet air temperature for example in a fluid bed dryer until the desired loss on drying value in the range of 1-3% is obtained;

f. delumping the dried granulate for example by sieving through a sieve with a mesh size of 0.6 mm-1.6 mm, preferably 1.0 mm; and g. adding preferably sieved lubricant to the granulate for final blending for example in a cube mixer.

In an alternative process part of the excipients such as part of a disintegrant (e.g. corn starch) or a diluent (e.g. pregelatinized starch) or an additional disintegrant (crospovidone) can be added extragranular prior to final blending of step g.

In another alternative version of the process the granulate produced in steps a to e is produced in a one pot high shear granulation process and subsequent drying in a one pot granulator.

For the preparation of capsules the final blend is further filled into capsules.

For the preparation of tablets or tablet cores the final blend is further compressed into tablets of the target tablet core weight with appropriate size and crushing strength, using an appropriate tablet press.

For the preparation of film-coated tablets a coating suspension is prepared and the compressed tablet cores are coated with the coating suspension to a weight gain of about 2-4%, preferably about 3%, using a standard film coater. The film-coating solvent is a volatile component, which does not remain in the final product. To reduce the required amount of lubricant in the tablets it is an option to use an external lubrication system.

Fluid Bed Granulation

In the wet granulation process the granulation liquid is a solvent such as water, ethanol, methanol, isopropanol, acetone, preferably ethanol, and contains a binder such as copovidone. The solvent is a volatile component, which does not remain in the final product. The active ingredient and the other excipients with exception of the lubricant are premixed and granulated with the granulation liquid using a fluid bed granulator. The granulation step is followed by a dry sieving of the granules.

The dried granules are sieved through an appropriate sieve. After addition of the other excipients with exception of the lubricant the mixture is blended in a suitable conventional blender such as a free fall blender followed by addition of the lubricant such as magnesium stearate and final blending in the blender.

Thus an exemplary wet granulation process for the preparation of a pharmaceutical composition according to the present invention comprises
a. dissolving a binder such as copovidone in a solvent such as purified water at ambient temperature to produce a granulation liquid;
b. blending a compound of formula 1, a diluent, and a disintegrant in the fluid bed, to produce a pre-mix;
c. granulate the pre-mix with the granulation liquid in a fluid bed granulator;
d. performing the drying step of the granulate at about 40-75° C. and preferably 55-65° C. inlet air until the desired loss on drying value in the range of 1-3% is obtained;
e. delumping the dried granulate for example by sieving through a sieve with a mesh size of 0.6 mm-1.6 mm, preferably 1.0 mm; and
f. adding preferably sieved lubricant to the granulate for final blending for example in a cube mixer.

In an alternative process part of the excipients such as part of a disintegrant (e.g. corn starch) or a diluent (e.g. pregelatinized starch) or an additional disintegrant (crospovidone) can be added extragranular prior to final blending of step f.

For the preparation of capsules the final blend is further filled into capsules.

For the preparation of tablets or tablet cores the final blend is further compressed into tablets of the target tablet core weight with appropriate size and crushing strength, using an appropriate tablet press.

For the preparation of film-coated tablets a coating suspension is prepared and the compressed tablet cores are coated with the coating suspension to a weight gain of about 2-4%, preferably about 3%, using a standard film coater. The film-coating solvent is a volatile component, which does not remain in the final product. To reduce the required amount of lubricant in the tablets it is an option to use an external lubrication system.

Hot Melt Granulation

In the hot melt granulation process the binder is a melting agent such as polyethylene glycol, stearic acid, stearic-palmitic acid, poloxamer, glyceryl monostearate or polyethylene oxide. The active ingredient and the other excipients with exception of the lubricant are premixed and granulated with the binder using for example a high shear granulator. The granulation step is followed by a cooling step, and sieving of the granules.

The granules are sieved through an appropriate sieve. After addition of the other excipients with exception of the lubricant the mixture is blended in a suitable conventional blender such as a free fall blender followed by addition of the lubricant such as magnesium stearate and final blending in the blender.

Thus an exemplary hot melt granulation process for the preparation of a pharmaceutical composition according to the present invention comprises
a. blending a compound of formula 1, a diluent, and a disintegrant in a suitable mixer, to produce a pre-mix;
b. heating the pre-mix and subsequently granulating the pre-mix for example in a high shear mixer;
c. cooling down the granulate at approx 28°;
d. delumping the granulate for example by sieving through a sieve with a mesh size of 0.6 mm-1.6 mm, preferably 1.0 mm; and
e. adding preferably sieved lubricant to the granulate for final blending for example in a cube mixer.

In an alternative process part of the excipients such as part of a disintegrant (e.g. corn starch) or a diluent (e.g. pregelatinized starch) or an additional disintegrant (crospovidone) can be added extragranular prior to final blending of step e.

In another alternative version of the process the granulate produced in steps a to c is produced in a one pot high shear granulation.

For the preparation of capsules the final blend is further filled into capsules.

For the preparation of tablets or tablet cores the final blend is further compressed into tablets of the target tablet core weight with appropriate size and crushing strength, using an appropriate tablet press.

For the preparation of film-coated tablets a coating suspension is prepared and the compressed tablet cores are coated with the coating suspension to a weight gain of about 2-4%, preferably about 3%, using a standard film coater. The film-coating solvent is a volatile component, which does not remain in the final product. To reduce the required amount of lubricant in the tablets it is an option to use an external lubrication system.

Roller Compaction

In the dry granulation process the active ingredient alone or the active ingredient together with the lubricant or the active ingredient and the diluent or a mixture of the diluent and the lubricant are premixed and compacted using a roller compactor. The dry granulation step is followed by one or two sieving steps.

The granules are sieved through an appropriate sieve. After addition of the other excipients with exception of the lubricant the mixture is blended in a suitable conventional blender such as a free fall blender followed by addition of the lubricant such as magnesium stearate and final blending in the blender.

Thus an exemplary dry granulation process for the preparation of a pharmaceutical composition according to the present invention comprises
a. blending a compound of formula 1, a diluent, and a lubricant in a suitable mixer, to produce a pre-mix;
b. compacting the pre-mix using a roller compactor;
c. sieving the granulated pre-mix through a sieve with a mesh size of at least 0.6 mm and preferably 0.8 mm;
d. delumping the granulate for example by sieving through a sieve with a mesh size of 0.6 mm-1.6 mm, preferably 1.0 mm;
e adding additional diluent and disintegrant and blend in a suitable blender; and
f. adding preferably sieved lubricant to the granulate for final blending for example in a cube mixer.

In an alternative process part of the excipients such as part of a disintegrant or a binder (copovidone) can be added intragranular prior to granulation of step b.

For the preparation of capsules the final blend is further filled into capsules.

For the preparation of tablets or tablet cores the final blend is further compressed into tablets of the target tablet core weight with appropriate size and crushing strength, using an appropriate tablet press.

For the preparation of film-coated tablets a coating suspension is prepared and the compressed tablet cores are coated with the coating suspension to a weight gain of about 2-4%, preferably about 3%, using a standard film coater. The film-coating solvent is a volatile component, which does not remain in the final product. To reduce the required amount of lubricant in the tablets it is an option to use an external lubrication system.

Hot Melt Extrusion

In the hot melt extrusion process the binder is a melting agent such as polyethylene glycol, stearic acid, stearic-palmitic acid, poloxamer, vitamin E TGPS, glyceryl monostearate or polyethylene oxide. The active ingredient and the other excipients with exception of the lubricant are premixed and granulated with the binder using an extruder. The granulation step is followed by a cooling step, and sieving of the granules.

The granules are sieved through an appropriate sieve. After addition of the other excipients with exception of the lubricant the mixture is blended in a suitable conventional blender such as a free fall blender followed by addition of the lubricant such as magnesium stearate and final blending in the blender.

Thus an exemplary hot melt extrusion process for the preparation of a pharmaceutical composition according to the present invention comprises a. blending a compound of formula 1 and a binder in a suitable mixer, to produce a pre-mix;
b. granulating the heated pre-mix in an extruder;
c. optionally sieving the granulated pre-mix through a sieve with a mesh size of at least 1.0 mm and preferably 3 mm;
d. delumping the granulate for example by sieving through a sieve with a mesh size of 0.6 mm-1.6 mm, preferably 1.0 mm;
e. and adding a diluent and a disintegrant and blending in a suitable blender; and
f. adding preferably sieved lubricant to the granulate for final blending for example in a cube mixer.

In an alternative process part of the excipients such as part of a disintegrant or a diluent or an additional disintegrant can be added intragranular prior to extrusion of step b.

For the preparation of capsules the final blend is further filled into capsules.

For the preparation of tablets or tablet cores the final blend is further compressed into tablets of the target tablet core weight with appropriate size and crushing strength, using an appropriate tablet press.

For the preparation of film-coated tablets a coating suspension is prepared and the compressed tablet cores are coated with the coating suspension to a weight gain of about 2-4%, preferably about 3%, using a standard film coater. The film-coating solvent is a volatile component, which does not remain in the final product. To reduce the required amount of lubricant in the tablets it is an option to use an external lubrication system.

EXAMPLES

The present invention is directed to the use of compounds of formula 1 for the preparation of pharmaceutical formulations for the treatment of diseases connected with the CCR3 receptor. A CCR3 receptor binding test showing this activity was already disclosed in WO 2010 115836. Ki values for the compounds of formula 1 (human Eotaxin-1 at human CCR3-Receptor) are shown in the table below. As used herein, "activity" is intended to mean a compound demonstrating an inhibition of 50% at µM or higher in inhibition when measured in the aforementioned assays. Such a result is indicative of the intrinsic activity of the compounds as inhibitor of CCR3 receptor activity.

The examples of compounds of formula 1 can be synthesized according to the description of WO 2010 115836, which is herewith incorporated by reference. The salts of these examples can be formed by crystallizing the free bases from a solution containing HCl. Preferably the examples 1, 2 3, 4, 5, 6, 7, 8, 9 and 10 are in form of the dihydrochloride.

| # | Structure | hCCR3 Ki (nM) |
|---|-----------|---------------|
| 1. | 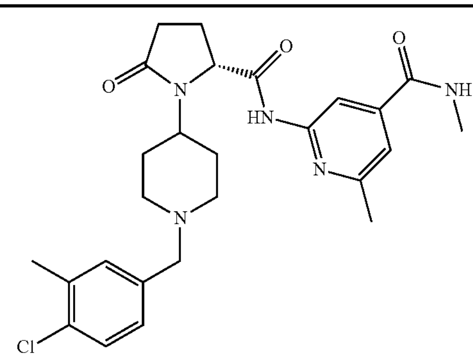 | 10.4 |
| 2. | 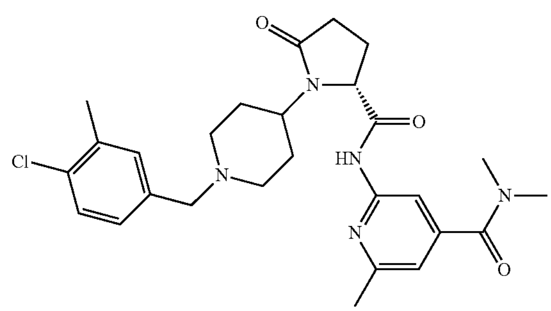 [SMILES: Cc1cc(C(=O)N(C)C)cc(NC(=O)[C@H]2CCC(=O)N2C2CCN(Cc3ccc(Cl)c(C)c3)CC2)n1] | 3.2 |

-continued
| # | Structure | hCCR3 Ki (nM) |
|---|---|---|
| 3. | 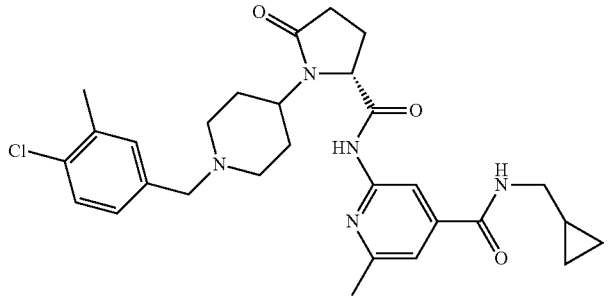 [SMILES: Cc1cc(C(=O)NCC2CC2)cc(NC(=O)[C@H]2CCC(=O)N2C2CCN(Cc3ccc(Cl)c(C)c3)CC2)n1] | 3.5 |
| 4. | 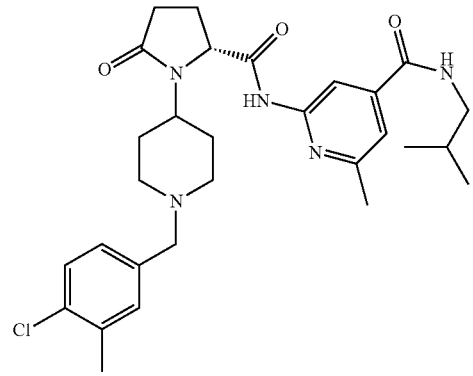 [SMILES: Cc1cc(C(=O)NCC(C)C)cc(NC(=O)[C@H]2CCC(=O)N2C2CCN(Cc3ccc(Cl)c(C)c3)CC2)n1] | 4.3 |
| 5. | 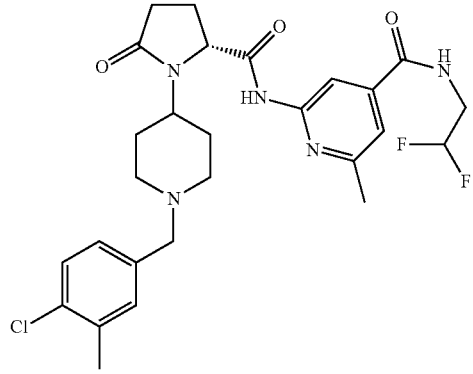 [SMILES: Cc1cc(C(=O)NCC(F)F)cc(NC(=O)[C@H]2CCC(=O)N2C2CCN(Cc3ccc(Cl)c(C)c3)CC2)n1] | 4.6 |
| 6. | 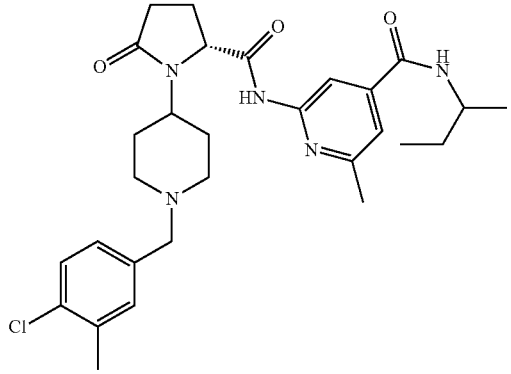 [SMILES: CCC(C)NC(=O)c1cc(C)nc(NC(=O)[C@H]2CCC(=O)N2C2CCN(Cc3ccc(Cl)c(C)c3)CC2)c1] | 4.0 |

-continued

| # | Structure | hCCR3 Ki (nM) |
|---|---|---|
| 7. | 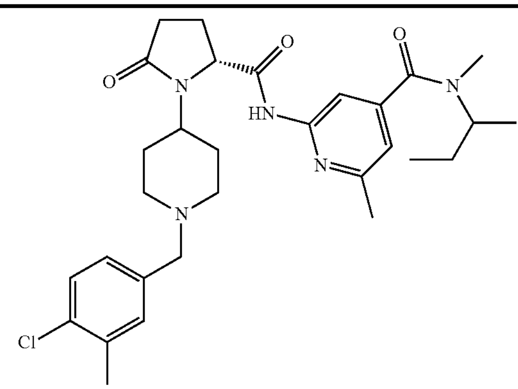 | 5.2 |
| 8. | 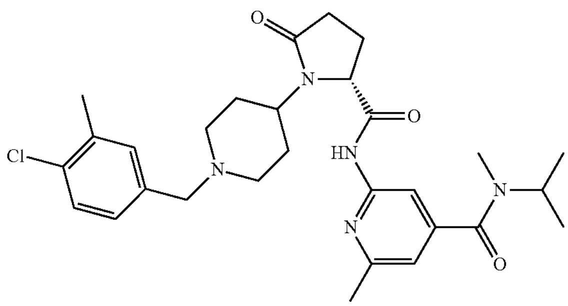 [SMILES: Cc1cc(C(=O)N(C)C(C)C)cc(NC(=O)[C@H]2CCC(=O)N2C2CCN(Cc3ccc(Cl)c(C)c3)CC2)n1] | 2.3 |
| 9. | 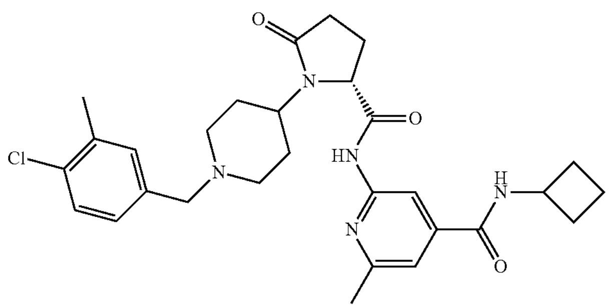 [SMILES: Cc1cc(C(=O)NC2CCC2)cc(NC(=O)[C@H]2CCC(=O)N2C2CCN(Cc3ccc(Cl)c(C)c3)CC2)n1] | 4.2 |
| 10. | 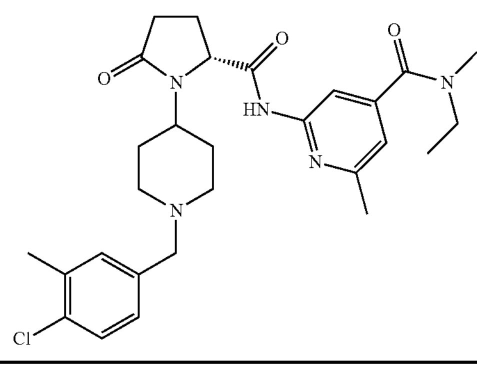 | 1.7 |

Example for Degradation

High Performance Liquid Chromatography (HPLC) with a reversed phase column and a gradient with buffer/acetonitrile and UV quantification were used for the quantification of degradation products The stability results of storage under stress conditions (bottles at 40° C./60° C.) and open storage at 25° C./60% r.h. for pure drug substance and different tablet formulation provide evidence that due to the formulation significant stability improvement was achieved.

The drug substance stored open for one week at 25° C./60% r.h. liquefies, which is accompanied by degradation (total degradation of 2.5%). Stored in a close container for 3 months a total degradation of 43% was quantified.

The different formulation principles developed show under the same conditions and similar packaging no degradation (alu/alu blister no degradation product >0.1% after 3 month) and under open storage conditions at 25° C./60% r.h. (1 week) a total degradation of 0.7%.

According to internationally accepted guidelines (e.g. ICH Q3b) the improved stability characteristics enable the administration of the new chemical entity to patients.

Tablets

With the compounds above i.e. examples 1, 2, 3, 4, 5, 6, 7, 8, 9 and 10 in form of the hydrochloride or examples 1, 2 3, 4, 5, 6, 7, 8, 9 and 10 in form of the dihydrochloride the following non-limiting examples for solid pharmaceutical compositions can be made:

Example 1—Tablet Formulation—Wet Granulation

Copovidone is dissolved in ethanol at ambient temperature to produce a granulation liquid. An active CCR3 antagonist ingredient (one or more compound of formula 1), lactose and part of the crospovidone are blended in a suitable mixer, to produce a pre-mix. The pre-mix is moistened with the granulation liquid and subsequently granulated. The moist granulate is optionally sieved through a sieve with a mesh size of 1.6-3.0 mm. The granulate is dried at 45° C. in a suitable dryer to a residual moisture content corresponding to 1-3% loss on drying. The dried granulate is sieved through a sieve with a mesh size of 1.0 mm. The granulate is blended with part of the crospovidone and microcrystalline cellulose in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
| --- | --- | --- |
| Active ingredient | 28.500 | 30.0 |
| Crospovidone | 1.500 | 1.6 |
| Lactose | 28.000 | 29.5 |
| Copovidone | 3.000 | 3.2 |
| —>Total (granulate) | 61.000 | —>64.3 |
| Microcrystalline cellulose | 31.000 | 32.6 |
| Crospovidone | 2.500 | 2.6 |
| Magnesium stearate | 0.500 | 0.5 |
| Total | 95.000 | 100.000 |

Example 2—Tablet Formulation—Melt Granulation

An active CCR3 antagonist ingredient (one or more compound of formula 1), lactose, part of the mcc (microcrystalline cellulose), polyethylene glycole, lactose and part of the crospovidone are blended in a suitable mixer, to produce a pre-mix. The pre-mix is heated in a high shear mixer and subsequently granulated. The hot granulate is cooled down to room temperature and sieved through a sieve with a mesh size of 1.0 mm. The granulate is blended with part of the crospovidone and microcrystalline cellulose in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
| --- | --- | --- |
| Active ingredient | 28.500 | 30.0 |
| Crospovidone | 1.500 | 1.6 |
| Lactose | 11.000 | 11.6 |
| Polyethylene glycole | 14.300 | 15.1 |
| MCC | 5.700 | 6.0 |
| —>Total (granulate) | 61.000 | —>64.3 |
| Microcrystalline cellulose | 31.000 | 32.6 |
| Crospovidone | 2.500 | 2.6 |
| Magnesium stearate | 0.500 | 0.5 |
| Total | 95.000 | 100.000 |

Example 3—Tablet Formulation—Hot Melt Granulation

An active CCR3 antagonist ingredient (one or more compound of formula 1), mannit, polyethylene glycole and part of the crospovidone are blended in a suitable mixer, to produce a pre-mix. The pre-mix is heated in a high shear mixer and subsequently granulated. The hot granulate is cooled down to room temperature and sieved through a sieve with a mesh size of 1.0 mm. The granulate is blended with part of the crospovidone and mannit in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
| --- | --- | --- |
| Active ingredient | 28.500 | 30.0 |
| Crospovidone | 1.500 | 1.6 |
| Mannit | 16.700 | 17.6 |
| Polyethylene glycole | 14.300 | 15.1 |
| —>Total (granulate) | 61.000 | —>64.3 |
| Mannit | 31.000 | 32.6 |
| Crospovidone | 2.500 | 2.6 |
| Magnesium stearate | 0.500 | 0.5 |
| Total | 95.000 | 100.000 |

Example 4—Tablet Formulation—Hot Melt Extrusion

An active CCR3 antagonist ingredient (one or more compound of formula 1) and stearic-palmitic acid are blended in a suitable mixer, to produce a pre-mix. The pre-mix is extruded in a twin-screw-extruder and subsequently granulated. The granulate is sieved through a sieve with a mesh size of 1.0 mm. The granulate is blended with mannit and crospovidone in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
|---|---|---|
| Active ingredient | 28.500 | 30.0 |
| Stearic-palmitic acid | 27.500 | 28.9 |
| ->Total (granulate) | 56.000 | ->58.9 |
| Mannit | 32.600 | 34.3 |
| Crospovidone | 5.600 | 5.9 |
| Magnesium stearate | 0.800 | 0.9 |
| Total | 95.000 | 100.000 |

Example 5—Tablet Formulation—Hot Melt Extrusion

An active CCR3 antagonist ingredient (one or more compound of formula 1) and stearic-palmitic acid are blended in a suitable mixer, to produce a pre-mix. The pre-mix is extruded in a twin-screw-extruder and subsequently granulated. The granulate is sieved through a sieve with a mesh size of 1.0 mm. The granulate is directly filled into hard capsules. The following capsule composition can be obtained:

| Component | mg/tablet | %/tablet |
|---|---|---|
| Active ingredient | 70.000 | 70.0 |
| Stearic-palmitic acid | 30.000 | 30.0 |
| ->Total (granulate) | 100.000 | ->100.0 |
| Capsule | 90.000 | — |
| Total | 190.000 | 100.000 |

Example 6—Tablet Formulation—Roller Compaction

An active CCR3 antagonist ingredient (one or more compound of formula 1), part of mannit and crospovidone and magnesium stearate are blended in a suitable mixer, to produce a pre-mix. The pre-mix is compacted with a roller compactor and subsequently granulated. Optionally, the granulate is sieved through a sieve with a mesh size of 0.8 mm. The granulate is blended with part of mannit and crospovidone in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
|---|---|---|
| Active ingredient | 28.500 | 30.0 |
| Crospovidone | 1.400 | 1.5 |
| Mannit | 34.600 | 36.4 |
| Magnesium stearate | 0.500 | 0.5 |
| ->Total (granulate) | 65.000 | ->68.4 |
| Mannit | 27.000 | 28.4 |
| Copovidone | 1.600 | 1.7 |
| Crospovidone | 0.950 | 1.0 |
| Magnesium stearate | 0.450 | 0.5 |
| Total | 95.000 | 100.000 |

Example 7.1—Tablet Formulation—Roller Compaction

An active CCR3 antagonist ingredient (one or more compound of formula 1) and magnesium stearate are blended in a suitable mixer, to produce a pre-mix. The pre-mix is compacted with a roller compactor and subsequently granulated. Optionally, the granulate is sieved through a sieve with a mesh size of 0.8 mm. The granulate is blended with mannit and croscarmellose sodium in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
|---|---|---|
| Active ingredient | 114.200 | 66.0 |
| Magnesium stearate | 1.800 | 1.0 |
| ->Total (granulate) | 116.000 | ->67.0 |
| Mannit | 51.000 | 29.5 |
| Croscarmellose sodium | 3.500 | 2.0 |
| Magnesium stearate | 2.500 | 1.5 |
| Total | 173.000 | 100.000 |

Example 7.2—Tablet Formulation—Roller Compaction

An active CCR3 antagonist ingredient (one or more compound of formula 1) is compacted with a roller compactor and subsequently granulated. Optionally, the granulate is sieved through a sieve with a mesh size of 0.8 mm. The granulate is blended with dibasic calciumphosphate anhydrous, microcrystalline cellulose and croscarmellose sodium in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
|---|---|---|
| Active ingredient | 114.000 | 66.0 |
| Microcrystalline cellulose | 17.400 | 10.0 |
| Dibasic calciumphosphate | 32.100 | 18.5 |
| Croscarmellose sodium | 6.900 | 4.0 |
| Magnesium stearate | 2.600 | 1.5 |
| Total | 173.000 | 100.000 |

Example 8—Tablet Formulation—Roller Compaction

An active CCR3 antagonist ingredient (one or more compound of formula 1) and magnesium stearate are blended in a suitable mixer, to produce a pre-mix. The pre-mix is compacted with a roller compactor and subsequently granulated. Optionally, the granulate is sieved through a sieve with a mesh size of 0.8 mm. The granulate is blended with microcrystalline cellulose and crospovidone in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
|---|---|---|
| Active ingredient | 114.200 | 66.0 |
| Magnesium stearate | 1.800 | 1.0 |
| ->Total (granulate) | 116.000 | ->67.0 |
| MCC | 51.000 | 29.5 |
| Crospovidone | 3.500 | 2.0 |
| Magnesium stearate | 2.500 | 1.5 |
| Total | 173.000 | 100.000 |

Example 9.1—Coated Tablet Formulation

Tablet cores according above mentioned formulations can be used to produce film-coated tablets. Hydroxypropyl methylcellulose (HPMC), polyethylene glycol, talc, titanium dioxide and iron oxide are suspended in purified water in a suitable mixer at ambient temperature to produce a coating suspension. The tablet cores are coated with the coating suspension to a weight gain of about 3% to produce film-coated tablets. The following film coating composition can be obtained:

| Component | mg/tablet | %/tablet |
|---|---|---|
| Hypromellose (HPMC) | 2.40 | 48.0 |
| Polyethylene glycol 6000 | 0.70 | 14.0 |
| Titanium dioxide | 0.90 | 18.0 |
| Talcum | 0.90 | 18.0 |
| Iron oxide red | 0.10 | 2.0 |
| Purified water (volatile component) | — | — |
| Total | 5.00 | 100.0 |

Example 9.2—Coated Tablet Formulation

Tablet cores according above mentioned formulations can be used to produce film-coated tablets. Polyvinyl alcohol (PVA), polyethylene glycol, talc, titanium dioxide and iron oxide are suspended in purified water in a suitable mixer at ambient temperature to produce a coating suspension. The tablet cores are coated with the coating suspension to a weight gain of about 3% to produce film-coated tablets. The following film coating composition can be obtained:

| Component | mg/tablet | %/tablet |
|---|---|---|
| Polyvinyl alcohol (PVA) | 2.00 | 40.0 |
| Polyethylene glycol 6000 | 1.0 | 20.2 |
| Titanium dioxide | 1.11 | 22.1 |
| Talcum | 0.74 | 14.8 |
| Iron oxide red | 0.08 | 1.6 |
| Iron oxide yellow | 0.07 | 1.4 |
| Purified water (volatile component) | — | — |
| Total | 5.00 | 100.0 |

Indications

The compounds of formula 1 as described above are useful for manufacturing a pharmaceutical formulation for the prevention and/or treatment of diseases wherein the activity of a CCR3-receptor is involved.

Preferred is the manufacturing of a medicament for the prevention and/or treatment of a wide variety of inflammatory, infectious, and immunoregulatory disorders and diseases of the respiratory or gastrointestinal complaints, inflammatory diseases of the joints and allergic diseases of the nasopharynx, eyes, and skin, including asthma and allergic diseases, eosinophilic diseases, infection by pathogenic microbes (which, by definition, includes viruses), as well as autoimmune pathologies such as the rheumatoid arthritis and atherosclerosis, as well as diseases associated with abnormal enhanced neovascularization such as age-related macular degeneration (AMD), including dry age-related macular degeneration (dAMD) and wet age-related macular degeneration (wAMD); diabetic retinopathy and diabetic macular edema, retinopathy of prematurity (ROP), central retinal vein occlusion (CRVO), nasal polyposis, eosinophilic esophagitis, eosinophillic gastroenteritis (e.g. eosinophilic gastritis and eosinophilic ententeritis), hypereosinophilic syndrome and Churg Strauss syndrome.

Age-related macular degeneration is a leading cause of blindness worldwide. Most blindness in AMD results from invasion of the retina by choroidal neovascularization. CCR3 is specifically expressed in choroidal neovascular endothelial cells of AMD patients. In an often used mouse animal model for AMD laser injury-induced choroidal neovascularization was diminished by genetic depletion of CCR3 or CCR3 ligands as well as by treatment of the mice with an anti-CCR3 antibody or an CCR3 antagonist (Takeda et al, Nature 2009, 460(7252):225-30).

Most preferred is the manufacturing of a medicament for the prevention and/or treatment of e.g. inflammatory or allergic diseases and conditions, including respiratory allergic diseases such as asthma, perennial and seasonal allergic rhinitis, allergic conjunctivitis, hypersensitivity lung diseases, hypersensitivity pneumonitis, eosinophilic cellulites (e. g., Well's syndrome), eosinophilic pneumonias (e. g., Loeffler's syndrome, chronic eosinophilic pneumonia), eosinophilic fasciitis (e. g., Shulman's syndrome), delayed-type hypersensitivity, interstitial lung diseases (ILD) (e. g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); non-allergic asthma; Exercise induced bronchoconstriction; systemic anaphylaxis or hypersensitivity responses, drug allergies (e. g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, immune thrombocytopenia (adult ITP, neonatal thrombocytopenia, paediatric ITP), immune haemolytic anaemia (auto-immune and drug induced), Evans syndrome (platelet and red cell immune cytopaenias), Rh disease of the newborn, Goodpasture's syndrome (anti-GBM disease), Celiac, Auto-immune cardio-myopathy juvenile onset diabetes; glomerulonephritis, autoimmune thyroiditis, Behcet's disease; graft rejection (e. g., in transplantation), including allograft rejection or graftversus-host disease; inflammatory bowel diseases, such as Crohn's disease and ulcerative colitis; spondyloarthropathies; scleroderma; psoriasis (including Tcell mediated psoriasis) and inflammatory dermatoses such as an dermatitis, eczema, atopic dermatitis, allergic contact dermatitis, urticaria; vasculitis (e. g., necrotizing, cutaneous, and hypersensitivity vasculitis); erythema nodosum; eosinophilic myositis, eosinophilic fasciitis; cancers with leukocyte infiltration of the skin or organs; chronic obstructive pulmonary disease, age-related macular degeneration (AMD), diabetic retinopathy and diabetic macular edema.

In another aspect of the invention preferred is the manufacturing of a medicament for the prevention and/or treatment of diseases selected from age-related macular degeneration (AMD), including dry age-related macular degeneration (dAMD) and wet age-related macular degeneration (wAMD); diabetic retinopathy and diabetic macular edema; and retinopathy of prematurity (ROP).

The invention claimed is:

1. A method comprising administering a pharmaceutical composition comprising as an active ingredient one or more compounds of formula 1

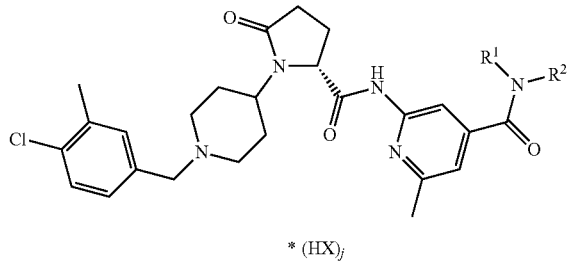

wherein
R$^1$ is H, C$_{1-6}$-alkyl, C$_{0-4}$-alkyl-C$_{3-6}$-cycloalkyl, or C$_{1-6}$-haloalkyl;
R$^2$ is H or C$_{1-6}$-alkyl;
X is chloride; and
j is 2,
a first diluent that is dibasic calcium phosphate anhydrous, a second diluent, a binder, a disintegrant and a lubricant.

2. The method according to claim 1, wherein
R$^1$ is H or Methyl; and
R$^2$ is H or Methyl.

3. The method according to claim 1, wherein the composition comprises an additional disintegrant.

4. The method according to claim 3, wherein the additional disintegrant is crospovidone.

5. The method according to claim 1, wherein the composition comprises a glidant.

6. The method according to claim 1, wherein the second diluent is cellulose powder, dibasic calcium phosphate dihydrate, erythritol, low substituted hydroxypropyl cellulose, mannitol, pregelatinized starch or xylitol.

7. The method according to claim 1, wherein the lubricant is talc, polyethyleneglycol, calcium behenate, calcium stearate, hydrogenated castor oil or magnesium stearate.

8. The method according to claim 1, wherein the binder is copovidone, hydroxypropyl methylcellulose, hydroxypropylcellulose, or polyvinylpyrrolidone.

9. The method according to claim 1, wherein the disintegrant is croscarmellose sodium.

10. The method according to claim 5, wherein the glidant is colloidal silicon dioxide.

11. The method according to claim 1, wherein the composition comprises

| | |
|---|---|
| 10-90% | active ingredient, |
| 5-70% | dibasic calcium phosphate anhydrous, |
| 5-30% | second diluent, |
| 0-30% | binder, |
| 1-12% | disintegrant, and |
| 0.1-3% | lubricant. |

12. The method according to claim 1, wherein the composition comprises

| | |
|---|---|
| 30-70% | active ingredient, |
| 10-75% | dibasic calcium phosphate anhydrous, |
| 5-30% | second diluent, |
| 0-30% | binder, |
| 0.5-20% | buffering agent, |
| 1-12% | disintegrant, and |
| 0.1-3% | lubricant. |

13. The method according to claim 1, wherein the composition is in the dosage form of a capsule, a tablet or a film-coated tablet.

14. The method of claim 13, wherein the dosage form comprises a 2-4% film coat.

15. The method of claim 14, wherein the film coat comprises a film-forming agent, a plasticizer, a glidant and optionally one or more pigments.

16. The method of claim 15, wherein the film coat comprises Polyvinyl alcohol (PVA) or hydroxypropylmethylcellulose (HPMC), polyethylene glycol (PEG), talc, titanium dioxide and iron oxide.

* * * * *

UNITED STATES PATENT AND TRADEMARK OFFICE
CERTIFICATE OF CORRECTION

PATENT NO. : 11,612,596 B2
APPLICATION NO. : 16/861473
DATED : March 28, 2023
INVENTOR(S) : Alfred Fetscher et al.

It is certified that error appears in the above-identified patent and that said Letters Patent is hereby corrected as shown below:

In the Specification

Please replace "p:" with -- pI: -- (Column 6, Line 52).

Please replace "products" with -- products. -- (Column 17, Line 64).

Please replace "glycole" with -- glycol -- (Column 19, Line 51).

Please replace "glycole" with -- glycol -- (Column 20, Line 6).

Please replace "glycole" with -- glycol -- (Column 20, Line 24).

Please replace "glycole" with -- glycol -- (Column 20, Line 43).

Please replace "eosinophillic" with -- eosinophilic -- (Column 24, Line 15).

Please replace "ententeritis" with -- enteritis -- (Column 24, Line 16).

Signed and Sealed this
Eleventh Day of July, 2023

Katherine Kelly Vidal
*Director of the United States Patent and Trademark Office*